United States Patent [19]

Litterer et al.

[11] Patent Number: 4,487,971
[45] Date of Patent: Dec. 11, 1984

[54] PROCESS FOR THE ISOLATION OF CRYSTALLINE 1,3-CYLOHEXANEDIONE

[75] Inventors: Heinz Litterer, Wiesbaden; Helmut Meidert, Frankfurt am Main, both of Fed. Rep. of Germany

[73] Assignee: Hoechst Aktiengesellschaft, Frankfurt am Main, Fed. Rep. of Germany

[21] Appl. No.: 537,648

[22] Filed: Sep. 30, 1983

[30] Foreign Application Priority Data

Oct. 4, 1982 [DE] Fed. Rep. of Germany ....... 3236700
Oct. 4, 1982 [DE] Fed. Rep. of Germany ....... 3236701

[51] Int. Cl.$^3$ ............................................. C07C 45/81
[52] U.S. Cl. .................................................... 568/366
[58] Field of Search ................ 568/354, 366, 410, 411

[56] References Cited

U.S. PATENT DOCUMENTS 2,554,980  5/1951  Fauque ................................. 568/410
4,041,049  8/1977  Muller et al. ........................ 568/354
4,335,261  6/1982  Ueda .................................... 568/366

FOREIGN PATENT DOCUMENTS 47806  6/1978  Japan .................................... 568/410

Primary Examiner—James H. Reamer
Attorney, Agent, or Firm—Curtis, Morris & Safford

[57] ABSTRACT

The invention provides a process for the isolation of crystalline 1,3-cyclohexanedione from the crude product formed in the catalytic gaseous phase cyclization of 5-oxohexanoic acid. Before or directly after condensation an auxiliary component consisting of at least one compound selected from the group consisting of cyclic hydrocarbons, chlorinated aliphatic hydrocarbons and monoethers is added to the crude product, subsequently the mixture of crude product and auxiliary component is distilled under normal or reduced pressure until the reaction water is removed and the residual content of auxiliary component in the remaining concentrate has attained a defined value, and the precipitated crystalline 1,3-cyclohexanedione is filtered off. Alternatively, the auxiliary component added may be distilled off substantially completely. In this case, either the same or another of the compounds or compound mixtures indicated as auxiliary component must be added subsequently to the remaining concentrate interspersed with crystals in order to obtain a substantially complete precipitation of the 1,3-cyclohexanedione in the form of crystals and formation of a filterable crystal pulp.

Alternatively, the crude product may be heated after condensation and the crude crystallized product obtained optionally after cooling be mixed with the auxiliary component. The further work-up is as described above.

20 Claims, No Drawings

PROCESS FOR THE ISOLATION OF CRYSTALLINE 1,3-CYLOHEXANEDIONE

In the dehydrating cyclization of 5-oxohexanoic acid to 1,3-cyclohexanedione in the gaseous phase in the presence of solid bed catalysts, according to known processes (for example German Offenlegungsschrift No. 2,448,677) a product mixture—hereinafter generally called "crude product"—is obtained which in addition to the intended 1,3-cyclohexanedione contains mainly 6-methyl-3,4-dihydro-2-pyranone, unreacted 5-oxohexanoix acid and the water of reaction.

Isolation of pure, crystalline 1,3-cyclohexanedione from this crude product is extraordinarily difficult. For, after condensation of the crude product, the 1,3-cyclohexanedione is present either totally or substantially in dissolved form. Although the crude product crystallizes on standing to an increasing extent, a crystal pulp of honey-like consistency is formed which practically cannot be filtered within an industrially acceptable period of time. Moreover, the 1,3-cyclohexanedione contained in the crude product crystallizes to a very insufficient extent only and in heavily contaminated state.

When decreasing the viscosity of the above crystal pulp by addition of a diluent, it is observed that the crystalline 1,3-cyclohexanedione filtered off is contaminated with substantial amounts of crystalline 5-oxohexanoic acid hydrate.

In view of the difficulties as described it is not surprising that according to the literature the amount of 1,3-cyclohexanedione formed in the cyclization of 5-oxohexanoic acid was determined by gas chromatography only, while an industrially feasible process for the isolation of pure crystalline 1,3-cyclohexanedione from the crude product has not been described hitherto.

The object achieved by the present invention is to isolate pure, crystalline 1,3-cyclohexanedione with high yields and a sufficiently high filtration speed. A subject of the present invention is a process for the isolation of crystalline 1,3-cyclohexanedione from the crude product formed in the catalytic gaseous phase cyclization of 5-oxohexanoic acid, which comprises adding to the crude product before or directly after condensation from 20 to 200 weight %, relative to the crude product, of an auxiliary component consisting of at least one compound selected from the group consisting of cyclic hydrocarbons, chlorinated aliphatic hydrocarbons and monoethers; distilling then the mixture of crude product and auxiliary component at 0° to 80° C. under normal or reduced pressure until the water of reaction is removed and the content of auxiliary component in the remaining concentrate is from 5 to 50 weight %; and filtering off the precipitated crystalline 1,3-cyclohexanedione.

Distillation is preferably carried out at 10° to 40° C.; the distillation temperatures indicated being measured in the sump in all cases.

The cyclic hydrocarbons suitable as auxiliary component may be aromatic or cycloaliphatic, chlorinated or not, and they have generally up to 12 carbon atoms. Preferred are benzene, toluene, xylene, mesitylene, cumene, ethylbenzene, chlorobenzene, dichlorobenzene, tetralin, decalin, cyclohexane or methylcyclohexane. Especially preferred are xylene, mesitylene, cumene, ethylbenzene, chlorobenzene, dichlorobenzene, tetralin or decalin.

The chlorinated aliphatic hydrocarbons have generally up to 6 carbon atoms. Preferred are methylene chloride, chloroform, carbon tetrachloride, dichloroethane, tetrachloroethane or butyl chloride; tetrachloroethane being especially preferred.

The monoethers may be aliphatic or aromatic; they have generally up to 12 carbon atoms. Preferred are diisopropyl ether, di-n-butyl ether or di-n-hexyl ether, anisol and phenetol; di-n-butyl ether being especially preferred.

The auxiliary components best suitable for xylene and di-n-butyl ether.

The auxiliary component is added in an amount of from 20 to 200, preferably 20 to 100, especially 20 to 80, weight % relative to the crude product; the optimum percental amount within these limits depending on the water content of the crude product and the water content of the azeotropic mixture of water and auxiliary component used. For example, under otherwise identical conditions an azeotropic mixture water/xylene contains about 10 times more water than an azeotropic mixture water/diisopropyl ether.

It is advantageous to mix the product current formed in the cyclization of 5-oxohexanoic acid which leaves the reactor in gaseous form with the auxiliary component immediately after the condensation, or to condense the gaseous product current directly in the auxiliary component, preferably at a temperature of up to 20° C. In an especially advantageous embodiment of the invention, gaseous product current and liquid auxiliary component are united at the reactor outlet before completely condensing this mixture. This is especially important for a continuous operation.

Alternatively, the auxiliary component added may of course be distilled off substantially completely from the 1,3-cyclohexanedione instead of stopping the distillation at the above residual content of from 5 to 50 weight %. In this case, either the same or another of the compounds or compound mixtures indicated as auxiliary component must be added subsequently to the remaining concentrate interspersed with crystals in order to obtain a substantially complete precipitation of the 1,3-cyclohexanedione in the form of crystals and formation of a filterable crystal pulp.

A further subject of the present invention is therefore a process for the isolation of crystalline 1,3-cyclohexanedione from the crude product formed in the catalytic gaseous phase cyclization of 5-oxohexanoic acid, which comprises adding to the crude product before or directly after condensation from 10 to 100 weight %, relative to the crude product, of an auxiliary component consisting of at least one compound selected from the group consisting of cyclic hydrocarbons, chlorinated aliphatic hydrocarbons and monoethers; distilling then the mixture of crude product and auxiliary component at 0° to 80° C. under normal or reduced pressure at least until the water of reaction is removed, then mixing the remaining concentrate with such an amount of an auxiliary component of the cited kind that the proportion of the latter in the mixture is from 5 to 50 weight %, and filtering off the precipitated crystalline 1,3-cyclohexanedione.

This process is hereinafter called also "two-step process" because auxiliary component is added twice, contrary to the process described first, in which auxiliary component is added only once, and which is hereinafter called also "single-step process".

In the two-step process, the amount of auxiliary component added before or directly after condensation of the crude product is preferably from 20 to 80, especially 20 to 60, weight % relative to the crude product; the optimum percental amount depending also in this case on the water content of the crude product and the water content of the azeotropic mixture which forms.

Preferred are likewise the auxiliary components cited as being preferred for the single-step process. In this case, however, toluene and xylene are especially preferred.

The temperature of the subsequent distillation is preferably from 10° to 40° C. To the concentrate thus formed, preferably an amount of auxiliary component is added which ensures that its proportion in the mixture which forms is from 10 to 30 weight %.

Advantageously, condensation of the gaseous product current is carried out as described for the single-step process.

The advantage of the two-step process resides in the fact that the optimum amounts of auxiliary component for the separation of water and precipitation of the cyclohexanedione can be determined more easily than in the single-step process.

The two methods described so far are based on converting the product current leaving the reactor in gaseous form to a uniform condensate, either by condensation in one single recipient, or by condensation in several series-connected vessels and subsequent combination of the condensates, which united condensate is then processed further. Alternatively, however, the product current can be converted in a defined manner to two condensates of different composition which are then processed separately. For this purpose, the gaseous product is condensed in two or more series-connected recipients while adjusting the temperature of these vessels in such a manner that the 1,3-cyclohexanedione mainly condenses in the first vessel and the water of reaction substantially in the second and the following recipients, if any. This is achieved by adjusting the temperature of the first vessel to 20 to 80, preferably 20° to 60° C., and that of the second and the following recipients, if any, to −40° to +60° C., preferably 0° to 60° C. When operating with more than two vessels, the contents of the second one is generally united with the contents of the following recipient(s). Sometimes it is advantageous to reject the contents of the vessel(s) following the second one, or at least the contents of the last ones in the series of vessels containing mainly water. In any case, however, two condensates are obtained, a first one containing the contents of the first vessel, and a second one containing the contents of the second and optionally the following recipient(s). Since the first condensate is substantially free from water, the removal of water otherwise required can be renounced; such an amount of auxiliary component of the cited kind is added that its proportion in the mixture is from 5 to 50 weight %, and the crystalline 1,3-cyclohexanedione thus caused to precipitate is filtered off. The second condensate contains the substantial amount of reaction water and is worked up as described above by a single- or two-step addition of auxiliary component and removal of water; that is treated in the same manner (including the preferred measures taken) as the above uniform condensate of the total reaction product.

A further subject of the invention is therefore a process for the isolation of crystalline 1,3-cyclohexanedione from the crude product formed in the gaseous phase cyclization of 5-oxohexanoic acid, which comprises obtaining a first condensate from the gaseous crude product by cooling to 20° to 80° C. and a second condensate by subsequent cooling of the remaining gas to −40° to +60° C., mixing then the first condensate with such an amount of an auxiliary component that the proportion of the latter in the mixture is from 5 to 50 weight %; the auxiliary component consisting of at least one compound selected from the group consisting of cyclic hydrocarbons, chlorinated aliphatic hydrocarbons and monoethers; and filtering off the precipitated crystalline 1,3-cyclohexanedione, subsequently mixing the second condensate with 20 to 200 weight %, relative to the condensate, of an auxiliary component of the above kind, and distilling the mixture at 0° to 80° C. under normal or reduced pressure until the water of reaction is removed and the content of auxiliary component in the remaining concentrate is from 5 to 50 weight %, and filtering off the precipitated crystalline 1,3-cyclohexanedione.

A further subject of the invention is a process for the isolation of crystalline 1,3-cyclohexanedione from the crude product formed in the catalytic gaseous phase cyclization of 5-oxohexanoic acid, which comprises obtaining a first condensate from the gaseous crude product by cooling to 20° to 80° C. and a second condensate by subsequent cooling of the remaining gas to −40° to +60° C., mixing then the first condensate with such an amount of an auxiliary component that the proportion of the latter in the mixture is from 5 to 50 weight %; the auxiliary component consisting of at least one compound selected from the group consisting of cyclic hydrocarbons, chlorinated aliphatic hydrocarbons and monoethers; and filtering off the precipitated crystalline 1,3-cyclohexanedione, subsequently mixing the second condensate with 10 to 100 weight %, relative to the condensate, of an auxiliary component of the above kind, and distilling the mixture at 0° to 80° C. under normal or reduced pressure at least until the water of reaction is removed, mixing then the remaining concentrate with such an amount of an auxiliary component of the cited kind that the proportion of the latter in the mixture is from 5 to 50 weight %, and filtering off the precipitated crystalline 1,3-cyclohexanedione.

The crystalline 1,3-cyclohexanedione obtained according to one of the described methods is subsequently washed, preferably with one of the compounds or compound mixtures cited as auxiliary components. Toluene is particularly suitable.

In the four operation modes described above the crude product of the 5-oxohexanoic acid cyclization is mixed with the auxiliary component before or directly after the condensation.

Contrary thereto, in the following four operation modes the crude product is condensed and subsequently heated for a certain time. The so-called "crude crystallized product" so obtained (optionally after cooling) is then mixed with the auxiliary component and processed further.

A further subject of the present invention is therefore a process for the isolation of crystalline 1,3-cyclohexanedione from the crude product formed in the catalytic gaseous phase cyclization of 5-oxohexanoic acid, which comprises heating the crude product after the condensation for 0.5 to 20 hours at 20° to 80° C., mixing subsequently the crude crystallized product so obtained, optionally after cooling, with 20 to 150 weight %, relative to the crude crystallized product, of an auxiliary component consisting of at least one compound selected from the group consisting of cyclic hydrocarbons, chlorinated aliphatic hydrocarbons and monoethers; distilling then the mixture of crude crystalline product and auxiliary component at 0° to 80° C. under normal or reduced pressure until the water of reaction is removed and the content of auxiliary component in the remaining concentrate is from 5 to 50 weight %; and filtering off the precipitated crystalline 1,3-cyclohexanedione.

Distillation is preferably carried out at 10° to 40° C.; the distillation temperatures indicated being measured in the sump in all cases.

The crude product is heated to 20° to 80° C., preferably 20° to 60° C., especially 30° to 50° C. The time of heating is from 0.5 to 20, preferably 1 to 12, especially 2 to 10, hours.

The cyclic hydrocarbons suitable as auxiliary component may be aromatic or cycloaliphatic, chlorinated or not, and they have generally up to 12 carbon atoms. Preferred are benzene, toluene, xylene, mesitylene, cumene, ethylbenzene, chlorobenzene, dichlorobenzene, tetralin, decalin, cyclohexane or methylcyclohexane. Especially preferred are xylene, mesitylene, cumene, ethylbenzene, chlorobenzene, dichlorobenzene, tetralin or decalin.

The chlorinated aliphatic hydrocarbons have generally up to 6 carbon atoms. Preferred are methylene chloride, chloroform, carbon tetrachloride, dichloroethane, tetrachloroethane or butyl chloride; tetrachloroethane being especially preferred.

The monoethers may be aliphatic or aromatic; they have generally up to 12 carbon atoms. Preferred are diisopropyl ether, di-n-butyl ether or di-n-hexyl ether, anisol and phenetol; di-n-butyl ether being especially preferred.

The auxiliary components best suitable are xylene and di-n-butyl ether.

The auxiliary component is added in an amount of from 20 to 150, preferably 20 to 80, especially 20 to 60, weight % relative to the crude crystallized product; the optimum percental amount within these limits depending on the water content of the crude crystallized product and the water content of the azeotropic mixture of water and auxiliary component used. For example, under otherwise identical conditions an azeotropic mixture water/xylene contains about 10 times more water than an azeotropic mixture water/diisopropyl ether.

Alternatively, the auxiliary component added may of course be distilled off substantially completely from the 1,3-cyclohexanedione instead of stopping the distillation at the above residual content of from 5 to 50 weight %. In this case, either the same or another of the compounds or compound mixtures indicated as auxiliary component must be added subsequently to the remaining concentrate interspersed with crystals in order to obtain a substantially complete precipitation of the 1,3-cyclohexanedione in the form of crystals and formation of a filterable crystal pulp.

A further subject of the present invention is therefore a process for the isolation of crystalline 1,3-cyclohexanedione from the crude product formed in the catalytic gaseous phase cyclization of 5-oxohexanoic acid, which comprises heating the crude product after the condensation for 0.5 to 20 hours at 20° to 80° C., mixing subsequently the crude crystallized product so obtained, optionally after cooling, with 10 to 100 weight %, relative to the crude crystallized product, of an auxiliary component consisting of at least one compound selected from the group consisting of cyclic hydrocarbons, chlorinated aliphatic hydrocarbons and monoethers; distilling then the mixture of crude crystallized product and auxiliary component at 0° to 80° C. under normal or reduced pressure at least until the water of reaction is removed, then mixing the remaining concentrate with such an amount of an auxiliary component of the cited kind that the proportion of the latter in the mixture is from 5 to 50 weight %, and filtering off the precipitated crystalline 1,3-cyclohexanedione.

This process is hereinafter called also "two-step process for crude crystallized product" because auxiliary component is added twice, contrary to the process described first, in which auxiliary component is added only once, and which is hereinafter called also "single-step process for crude crystallized product".

In the two-step process for crude crystallized product, the amount of auxiliary component added after condensation of the crude product is preferably from 20 to 70, especially 20 to 50, weight % relative to the crude crystallized product; the optimum percental amount depending also in this case on the water content of the crude crystallized product and the water content of the azeotropic mixture which forms.

Preferred are likewise the auxiliary components cited as being preferred for the single-step process for crude crystallized product. In this case, however, toluene and xylene are espe-crudecially preferred.

The temperature of the subsequent distillation is preferably from 10° to 40° C. To the concentrate thus formed, preferably an amount of auxiliary component is added which ensures that its proportion in the mixture which forms is from 10 to 30 weight %.

The advantage of the two-step process for crude crystallized product resides in the fact that the optimum amounts of auxiliary component for the separation of water and precipitation of the cyclohexanedione can be determined more easily than in the single-step process for crude crystallized product.

The two methods described so far are based on converting the product current leaving the reactor in gaseous form to a uniform condensate, either by condensation in one single recipient, or by condensation in several series-connected vessels and subsequent combination of the condensates, which united condensate is then processed further. Alternatively, however, the product current can be converted in a defined manner to two condensates of different composition which are then processed separately. For this purpose, the gaseous product is condensed in two or more series-connected recipients while adjusting the temperature of these vessels in such a manner that the 1,3-cyclohexanedione mainly condenses in the first vessel and the water of reaction substantially in the second and the following recipients, if any. This is achieved by adjusting the temperature of the first vessel to 20 to 80, preferably 20° to 60° C., and that the second and the following recipients, if any, to −40° to +60° C., preferably 0° to 60° C. When operating with more than two vessels, the contents of the second one is generally united with the contents of the following recipient(s). Sometimes it is advantageous to reject the contents of the vessel(s) following the second one, or at least the contents of the last ones in the series of vessels containing mainly water. In any case, however, two condensates are obtained, a first one containing the contents of the first vessel, and a second one containing the contents of the second and optionally the following recipient(s). Since the first condensate is substantially free from water, the removal of water otherwise required can be renounced; such an amount of auxiliary component of the cited kind is added that its proportion in the mixture is from 5 to 50 weight %, and the crystalline 1,3-cyclohexanedione thus caused to precipitate is filtered off. The second condensate contains the substantial amount of reaction water and is heated as described above. The crude crystallized product obtained is worked up by a single- or two-step addition of auxiliary component and removal of water; that is treated in the same manner (including the preferred measures taken) as the above uniform condensate of the total reaction product.

A further subject of the invention is therefore a process for the isolation of crystalline 1,3-cyclohexanedione from the crude product formed in the gaseous phase cyclization of 5-oxohexanoic acid, which comprises obtaining a first condensate from the gaseous crude product by cooling to 20° to 80° C. and a second condensate by subsequent cooling of the remaining gas to −40° to +60° C., mixing then the first condensate with such an amount of an auxiliary component that the proportion of the latter in the mixture is from 5 to 50 weight %; the auxiliary component consisting of at least one compound selected from the group consisting of cyclic hydrocarbons, chlorinated aliphatic hydrocarbons and monoethers; and filtering off the precipitated crystalline 1,3-cyclohexanedione, subsequently heating the second condensate for 0.5 to 20 hours to 20° to 80° C., mixing the crude crystallized product, optionally after cooling, with 20 to 150 weight %, relative to the crude crystallized product, of an auxiliary component of the above kind, and distilling the mixture at 0° to 80° C. under normal or reduced pressure until the water of reaction is removed and the content of auxiliary component in the remaining concentrate is from 5 to 50 weight %, and filtering off the precipitated crystalline 1,3-cyclohexanedione.

A further object of the invention is a process for the isolation of crystalline 1,3-cyclohexanedione from the crude product formed in the catalytic gaseous phase cyclization of 5-oxohexanoic acid, which comprises obtaining a first condensate from the gaseous crude product by cooling to 20° to 80° C. and a second condensate by subsequent cooling of the remaining gas to −40° to +60° C., mixing then the first condensate with such an amount of an auxiliary component that the proportion of the latter in the mixture is from 5 to 50 weight %; the auxiliary component consisting of at least one compound selected from the group consisting of cyclic hydrocarbons, chlorinated aliphatic hydrocarbons and monoethers; and filtering off the precipitated crystalline 1,3-cyclohexanedione, subsequently heating the second condensate for 0.5 to 20 hours to 20° to 80° C., mixing the crude crystallized product, optionally after cooling, with 10 to 100 weight %; relative to the crude crystallized product, of an auxiliary component of the above kind, and distilling the mixture at 0° to 80° C. under normal or reduced pressure at least until the water of reaction is removed, mixing then the remaining concentrate with such an amount of an auxiliary component of the cited kind that the proportion of the latter in the mixture is from 5 to 50 weight %, and filtering off the precipitated crystalline 1,3-cyclohexanedione.

The crystalline 1,3-cyclohexanedione obtained according to one of the described methods is subsequently washed, preferably with one of the compounds or compound mixtures cited as auxiliary components. Toluene is particularly suitable.

The following examples illustrate the invention. The percentages are by weight in all cases.

EXAMPLE 1

5-Oxohexanoic acid is passed at 380° C. under a nitrogen current over a crystalline aluminosilicate having a LHSV ($h^{-1}$) of 2.0. The molar ratio 5-oxohexanoic acid:$N_2$ is 1:4. The crude product (1.3 kg, cyclohexanedione proportion 40%) is taken up in 500 ml (=33.5% relative to crude product) of toluene, and this mixture is introduced into a 4 liter four-necked flask provided with a stirrer and descending condenser. This mixture is composed as follows: 25% toluene, 30% 1,3-cyclohexanedione, 14% 6-methyl-3,4-dihydro-2-pyranone, 8% water, 18% 5-oxohexanoic acid and about 5% by-products. At about 3 mbar and a bath temperature of 40° C., water with toluene is first distilled off with stirring until the sump temperature rises to 35° C. towards the end of the distillation.

Subsequently, 285 ml of toluene are stirred at room temperature into the light yellow, partially crystallized residue (990 g). The suspension obtained is allowed to stand for 4 to 5 hours at 0° C., and the crystal pulp is thoroughly suction-filtered via a glass filter funnel (for about 20 minutes). The filter cake is covered in the funnel with 250 ml of toluene, and then again thoroughly suction-filtered. It is then intensely stirred with 600 ml of toluene, the washing liquid is again suction-filtered, and the whole operation is repeated with the same amount of toluene.

After drying, the nearly colorless product has a weight of 444 g, the content of cyclohexanedione is 98.8%, that of oxohexanoic acid is 0.6%. Thus, 84.4% of the 1,3-cyclohexanedione present in the crude product are isolated in the form of crystals.

EXAMPLE 2

5-Oxohexanoic acid is reacted at 350° C., but otherwise as described in Example 1. The crude product (1.3 kg, cyclohexanedione proportion 34%) is taken up in 1,000 ml (=59.2% relative to crude product) of dibutyl ether, and the mixture is introduced into a 4 liter four-necked flask provided with stirrer and descending condenser. This mixture is composed as follows: 37.5% dibutyl ether, 21% 1,3-cyclohexanedione, 10% 6-methyl-3,4-dihydro-2-pyranone, 5% water, 22% 5-oxohexanoic acid and about 4% by-products. From this mixture, 800 ml of dibutyl ether together with the reaction water are distilled off at about 10 mbar, a bath temperature of 50° C. and a maximum sump temperature of 40° C.

The light yellow, partially crystallized residue (1,190 g) is allowed to stand at 0° C. for 4 to 5 hours, and the crystal pulp is then thoroughly suction-filtered via a glass filter funnel (for about 20 minutes).

In the funnel, the filter cake is first covered by 200 ml of toluene, and then again thoroughly suction-filtered. It is then intensely stirred with 500 ml of toluene, the washing liquid is again suction-filtered, and this operation is subsequently repeated using the same amount of toluene.

After drying, the nearly colorless product has a weight of 336 g, the content of cyclohexanedione is 99.1%, that of oxohexanoic acid is 0.4%. Thus 75.3% of the 1,3-cyclohexanedione present in the crude product are isolated in the form of crystals.

COMPARATIVE EXAMPLE 1

250 g of crude product (cyclohexanedione proportion 40%) completely crystallized after a 6 hours' standing are homogenized by stirring to give a crystal pulp which subsequently is thoroughly suction-filtered via a glass filter funnel. Due to the high viscosity of the mother liquor, this takes 3 to 4 hours. The crystalline filter cake is stirred with 70 ml of toluene, again suction-filtered, and the washing is then repeated using the same amount of toluene.

The yellowish crystalline product has a weight of 45 g after drying, the cyclohexanedione content is 94%. Thus, 42.3% only of the 1,3-cyclohexanedione present in the crude product can be isolated, moreover in a contaminated form: the product contains still 5% of 5-oxohexanoic acid.

COMPARATIVE EXAMPLE 2

Operations are as in Comparative Example 1, with the exception that the crystalline filter cake is washed twice with 70 ml of carbon tetrachloride instead of toluene.

After drying, the yellowish crystalline product has a weight of 59 g, the cyclohexanedione content is 82%. Thus, 48.3% only of the 1,3-cyclohexanedione present in the crude product can be isolated in this contaminated form; the product contains still 16% of 5-oxohexanoic acid.

COMPARATIVE EXAMPLE 3

Operations are as in Example 1; however, the crude product taken up in toluene is not subjected to dehydration but stored at room temperature. After a several days' standing, no precipitation of crystals can be observed.

EXAMPLE 3

5-Oxohexanoic acid is passed at 380° C. under a nitrogen current over a crystalline aluminosilicate having a LHSV ($h^{-1}$) of 2.0. The molar ratio 5-oxohexanoic acid:$N_2$ is 1:4. The crude product (1,3 kg, cyclohexanedione proportion 40%) is maintained at 40° C. for 4 hours with stirring and subsequently mixed with 375 ml of toluene (=25% relative to the crude product). This mixture is composed as follows: 20% toluene, 32% 1,3-cyclohexanedione, 0.5% 6-methyl-3,4-dihydro-2-pyranone, 5% water, 38% 5-oxohexanoic acid and about 4% by-products. At about 3 mbar and a bath temperature of 45° C., water and toluene are distilled off first until the sump temperature rises to 38° C. towards the end of the distillation.

Subsequently, 325 ml of toluene are stirred at room temperature into the light yellow, partially crystallized residue (1,085 g). The suspension obtained is allowed to stand for 4 to 5 hours at 0° C., and the crystal pulp is then thoroughly suction-filtered via a glass filter funnel (for about 40 minutes).

The filter cake is covered in the funnel with 250 ml of toluene, and again thoroughly suction-filtered. It is then intensely stirred with 500 ml of toluene, and the operation is repeated subsequently using the same amount of toluene.

After drying, the nearly colorless product has a weight of 377 g, the cyclohexanedione content is 98.2%, that of oxohexanoic acid is 1.4%. Thus, 71.2% of the 1,3-cyclohexanedione present in the crude product are isolated in the form of crystals.

EXAMPLE 4

5-Oxohexanoic acid is reacted as in Example 3. The crude product (1.3 kg, cyclohexanedione proportion 40%) is maintained for 4 hours at 40° C. with stirring and subsequently mixed with 850 ml of xylene (=57.6% relative to the crude product). This mixture is composed as follows: 36.5% xylene, 25.4% 1,3-cyclohexanedione, 0.6% 6-methyl-3,4-dihydro-2-pyranone, 4% water, 29% 5-oxohexanoic acid and about 4% by-products.

From this mixture, 600 ml of xylene and the water of reaction are distilled off at about 10 mbar, a bath temperature of 45° C. and a maximum sump temperature of 40° C.

The light yellow, partially crystallized residue (1,215 g) is allowed to stand for 4 to 5 hours at 0° C., and the crystal pulp is then thoroughly suction-filtered via a glass filter funnel (for about 45 minutes).

The filter cake is covered in the funnel by 200 ml of toluene, and again thoroughly suction-filtered. Subsequently, it is intensely stirred with 550 ml of toluene, which operation is repeated using the same amount of toluene.

After drying, the nearly colorless product has a weight of 382 g, the cyclohexanedione content is 98.3%, that of oxohexanoic acid is 1.2%. Thus, 72.2% of the 1,3-cyclohexanedione present in the crude product is isolated in crystalline form.

COMPARATIVE EXAMPLE 4

250 g of crude product (cyclohexanedione proportion 40%) completely crystallized after a six hours' standing are homogenized by stirring to give a crystal pulp which is then thoroughly suction-filtered via a glass filter funnel. Due to the high viscosity of the mother liquor, this takes 3 to 4 hours. The crystallized filter cake is stirred in 70 ml of toluene, again suction-filtered, and the washing is repeated using the same amount of toluene.

After drying, the yellowish crystalline product has a weight of 45 g, the cyclohexanedione content is 94%. Thus, 42.3% only of the 1,3-cyclohexanedione present in the crude product are isolated in this contaminated form; the product contains still 5% of 5-oxohexanoic acid.

COMPARATIVE EXAMPLE 5

Operations are as in Comparative Example 4, with the exception that the crystalline filter cake is washed twice with 70 ml of carbon tetrachloride.

After drying, the yellowish crystalline product has a weight of 59 g, the cyclohexanedione content is 82%. Thus, 48.3% only of the 1,3-cyclohexanedione present in the crude product can be isolated in this contaminated form; the product still contains 16% of 5-oxohexanoic acid.

What is claimed is:

1. A process for the isolation of crystalline 1,3-cyclohexanedione from the crude product formed in the catalytic gaseous phase cyclization of 5-oxohexanoic acid, which comprises adding to the crude product before or directly after condensation from to 20 to 200 weight %, relative to the crude product, of an auxiliary component consisting of at least one compound selected from the group consisting of cyclic hydrocarbons, chlorinated aliphatic hydrocarbons and monoethers; distilling then the mixture of crude product and auxiliary component at 0° to 80° C. under normal or reduced pressure until the water of reaction is removed and the content of auxiliary component in the remaining concentrate is from 5 to 50 weight %; and filtering off the precipitated crystalline 1,3-cyclohexanedione.

2. A process for the isolation of crystalline 1,3-cyclohexanedione from the crude product formed in the catalytic gaseous phase cyclization of 5-oxohexanoic acid, which comprises adding to the crude product before or directly after condensation from 10 to 100 weight %, relative to the crude product, of an auxiliary component consisting of at least one compound selected from the group consisting of cyclic hydrocarbons, chlorinated aliphatic hydrocarbons and monoethers; distilling then the mixture of crude product and auxiliary component at 0° to 80° C. under normal or reduced pressure at least until the water of reaction is removed, then mixing the remaining concentrate with such an amount of an auxiliary component of the cited kind that the proportion of the latter in the mixture is from 5 to 50 weight %, and filtering off the precipitated crystalline 1,3-cyclohexanedione.

3. A process for the isolation of crystalline 1,3-cyclohexanedione from the crude product formed in the gaseous phase cyclization of 5-oxohexanoic acid, which comprises obtaining a first condensate from the gaseous crude product by cooling to 20° to 80° C. and a second condensate by subsequent cooling of the remaining gas to −40° to +60° C., mixing then the first condensate with such an amount of an auxiliary component that the proportion of the latter in the mixture is from 5 to 50 weight %; the auxiliary component consisting of at least one compound selected from the group consisting of cyclic hydrocarbons, chlorinated aliphatic hydrocarbons and monoethers; and filtering off the precipitated crystalline 1,3-cyclohexanedione, subsequently mixing the second condensate with 20 to 200 weight %, relative to the condensate, of an auxiliary component of the above kind, and distilling the mixture at 0° to 80° C. under normal or reduced pressure until the water of reaction is removed and the content of auxiliary component in the remaining concentrate is from 5 to 50 weight %, and filtering off the precipitated crystalline 1,3-cyclohexanedione.

4. A process for the isolation of crystalline 1,3-cyclohexanedione from the crude product formed in the catalytic gaseous phase cyclization of 5-oxohexanoic acid, which comprises obtaining a first condensate from the gaseous crude product by cooling to 20° to 80° C. and a second condensate by subsequent cooling of the remaining gas to −40° to +60° C., mixing then the first condensate with such an amount of an auxiliary component with the proportion of the latter in the mixture is from 5 to 50 weight %; the auxiliary component consisting of at least one compound selected from the group consisting of cyclic hydrocarbons, chlorinated aliphatic hydrocarbons and monoethers; and filtering off the precipitated crystalline 1,3-cyclohexanedione, subsequently mixing the second condensate with 10 to 100 weight %, relative to the condensate, of an auxiliary component of the above kind, and distilling the mixture at 0° to 80° C. under normal or reduced pressure at least until the water of reaction is removed, mixing then the remaining concentrate with such an amount of an auxiliary component of the cited kind that the proportion of the latter in the mixture is from 5 to 50 weight %, and filtering off the precipitated crystalline 1,3-cyclohexanedione.

5. The process as claimed in claim 1, which comprises using xylene or di-n-butyl ether as auxiliary component.

6. The process as claimed in claim 2, which comprises using xylene or toluene as auxiliary component.

7. The process as claimed in claim 1, which comprises mixing the gaseous crude product directly after condensation with the auxiliary component, or condensing it in the auxiliary component.

8. The process as claimed in claim 1, which comprises uniting the gaseous crude product and the liquid component continuously at the reactor outlet, and subsequently condensing the mixture completely.

9. A process for the isolation of crystalline 1,3-cyclohexanedione from the crude product formed in the catalytic gaseous phase cyclization of 5-oxohexanoic acid, which comprises heating the crude product after the condensation for 0.5 to 20 hours at 20° to 80° C., mixing subsequently the crude crystallized product so obtained, optionally after cooling, with 20 to 150 weight %, relative to the crude crystallized product, of an auxiliary component consisting of at least one compound selected from the group consisting of cyclic hydrocarbons, chlorinated aliphatic hydrocarbons and monoethers; distilling then the mixture of crude crystalline product and auxiliary component at 0° to 80° C. under normal or reduced pressure until the water of reaction is removed and the content of auxiliary component in the remaining concentrate is from 5 to 50 weight %; and filtering off the precipitated crystalline 1,3-cyclohexanedione.

10. A process for the isolation of crystalline 1,3-cyclohexanedione from the crude product formed in the catalytic gaseous phase cyclization of 5-oxohexanoic acid, which comprises heating the crude product after the condensation for 0.5 to 20 hours at 20° to 80° C., mixing subsequently the crude crystallized product so obtained, optionally after cooling, with 10 to 100 weight %, relative to the crude crystallized product, of an auxiliary component consisting of at least one compound selected from the group consisting of cyclic hydrocarbons, chlorinated aliphatic hydrocarbons and monoethers; distilling then the mixture of crude crystallized product and auxiliary component at 0° to 80° C. under normal or reduced pressure at least until the water of reaction is removed, then mixing the remaining concentrate with such an amount of an auxiliary component of the cited kind that the proportion of the latter in the mixture is from 5 to 50 weight %, and filtering off the precipitated crystalline 1,3-cyclohexanedione.

11. A process for the isolation of crystalline 1,3-cyclohexanedione from the crude product formed in the gaseous phase cyclization of 5-oxohexanoic acid, which comprises obtaining a first condensate from the gaseous crude product by cooling to 20° to 80° C. and a second condensate by subsequent cooling of the remaining gas to −40° to +60° C., mixing then the first condensate with such an amount of an auxiliary component that the proportion of the latter in the mixture is from 5 to 50 weight %; the auxiliary component consisting of at least one compound selected from the group consisting of cyclic hydrocarbons, chlorinated aliphatic hydrocarbons and monoethers; and filtering off the precipitated crystalline 1,3-cyclohexanedione, subsequently heating the second condensate for 0.5 to 20 hours to 20° to 80° C., mixing the crude crystallized product, optionally after cooling, with 20 to 150 weight %, relative to the crude crystallized product, of an auxiliary component of the above kind, and distilling the mixture at 0° to 80°

C. under normal or reduced pressure until the water of reaction is removed and the content of auxiliary component in the remaining concentrate is from 5 to 50 weight %, and filtering off the precipitated crystalline 1,3-cyclohexanedione.

12. A process for the isolation of crystalline 1,3-cyclohexanedione from the crude product formed in the catalytic gaseous phase cyclization of 5-oxohexanoic acid, which comprises obtaining a first condensate from the gaseous crude product by cooling to 20° to 80° C. and a second condensate by subsequent cooling of the remaining gas to −40° to +60° C., mixing then the first condensate with such an amount of an auxiliary component that the proportion of the latter in the mixture is from 5 to 50 weight %; the auxiliary component consisting of at least one compound selected from the group consisting of cyclic hydrocarbons chlorinated aliphatic hydrocarbons and monoethers; and filtering off the precipitated crystalline 1,3-cyclohexanedione, subsequently heating the second condensate for 0.5 to 20 hours to 20° to 80° C., mixing the crude crystallized product, optionally after cooling, with 10 to 100 weight %, relative to the crude crystallized product, of an auxiliary component of the above kind, and distilling the mixture at 0° to 80° C. under normal or reduced pressure at least until the water of reaction is removed, mixing then the remaining concentrate with such an amount of an auxiliary component of the cited kind that the proportion of the latter in the mixture is from 5 to 50 weight %, and filtering off the precipitated crystalline 1,3-cyclohexanedione.

13. The process as claimed in claim 9, which comprises using xylene or di-n-butyl ether as auxiliary component.

14. The process as claimed in claim 10, which comprises using xylene or toluene as auxiliary component.

15. The process as claimed in claim 3, which comprises using xylene or di-n-butyl ether as auxiliary component.

16. The process as claimed in claim 4, which comprises using xylene or toluene as auxiliary component.

17. The process as claimed in claim 2, which comprises mixing the gaseous product directly after condensation with the auxiliary component or condensing it in the auxiliary component.

18. The process as claimed in claim 2, which comprises uniting the gaseous crude product and the liquid component continuously at the reactor outlet, and subsequently condensing the mixture completely.

19. The process as claimed in claim 11, which comprises using xylene or di-n-butyl ether as auxiliary component.

20. The process as claimed in claim 12, which comprises using xylene or toluene as auxiliary component.

* * * * *